US008816147B2

(12) United States Patent
Vinel et al.

(10) Patent No.: US 8,816,147 B2
(45) Date of Patent: Aug. 26, 2014

(54) PROCESS FOR SEPARATING 1-HEXENE FROM A MIXTURE OF PRODUCTS OBTAINED FROM AN ETHYLENE TRIMERIZATION ZONE (71) Applicant: AXENS, Rueil Malmaison Cedex (FR)

(72) Inventors: Daniel-Jean Vinel, Les Mureaux (FR); Jean-Alain Chodorge, Anthony (FR); Jerome Pigourier, Meudon (FR); Pierre-Yves Martin, Rueil Malmaison (FR); Laurent Bournay, Chaussan (FR)

(73) Assignee: Axens, Rueil-Malmaison Cedex (FR)

( * ) Notice: Subject to any disclaimer, the term of this patent is extended or adjusted under 35 U.S.C. 154(b) by 0 days.

(21) Appl. No.: 13/932,032

(22) Filed: Jul. 1, 2013

(65) Prior Publication Data
US 2014/0012059 A1   Jan. 9, 2014

(30) Foreign Application Priority Data

Jul. 4, 2012   (FR) ...................................... 12 01886

(51) Int. Cl.
*C07C 7/04* (2006.01)
(52) U.S. Cl.
CPC ........................................ *C07C 7/04* (2013.01)
USPC ............ 585/809; 585/802; 585/502; 585/508
(58) Field of Classification Search
None
See application file for complete search history.

(56) References Cited

U.S. PATENT DOCUMENTS

| | | | |
|---|---|---|---|
| 6,800,702 B2 * | 10/2004 | Wass | 526/124.3 |
| 2009/0326297 A1 | 12/2009 | Emoto et al. | |
| 2011/0288256 A1 * | 11/2011 | Vermeiren | 526/348.6 |
| 2013/0144024 A1 | 6/2013 | Lattner et al. | |

FOREIGN PATENT DOCUMENTS

| | | |
|---|---|---|
| EP | 2098542 A1 | 9/2009 |
| WO | 2011112184 A1 | 9/2011 |

OTHER PUBLICATIONS

Search Report from French Priority Application No. 12/01886 dated Feb. 28, 2013.

* cited by examiner

*Primary Examiner* — Tam M Nguyen
(74) *Attorney, Agent, or Firm* — Millen, White, Zelano & Branigan, P.C.

(57) ABSTRACT

A process for recovering 1-hexene comprising: a) separating the mixture obtained from the ethylene trimerization reaction into a top fraction comprising ethylene and a bottom fraction, b) separating a portion of the bottom fraction obtained from step a) into a top fraction comprising 1-hexene and 1-butene and a bottom fraction, c) separating a portion of the fraction comprising 1-hexene and 1-butene obtained from step b) into a top fraction principally comprising 1-butene and into a bottom fraction principally comprising 1-hexene, and in said process: a portion of the bottom fraction obtained from step b) is returned to the reaction section and another portion of said bottom fraction obtained from step b) is used in a recirculation loop connecting the reaction section and the column of said step b), said recirculation loop being used to cool the reaction section and to reboil said column of step b).

15 Claims, 2 Drawing Sheets

PROCESS FOR SEPARATING 1-HEXENE FROM A MIXTURE OF PRODUCTS OBTAINED FROM AN ETHYLENE TRIMERIZATION ZONE

FIELD OF THE INVENTION

The present invention relates to the production of 1-hexene, and more precisely to a process for the production and separation of 1-hexene from a mixture of products obtained from an ethylene trimerization zone.

The present invention also relates to a unit for the production and separation of 1-hexene, comprising an ethylene trimerization zone.

PRIOR ART 1-hexene can be produced with a high selectivity by oligomerizing ethylene, in particular by trimerizing ethylene in a catalytic system, in a generally homogeneous phase, in the presence or otherwise of a solvent. Despite the selectivity of the trimerization catalyst for the formation of 1-hexene, apart from unconverted ethylene, secondary products are formed by the reaction. The effluent obtained from ethylene trimerization may include alpha-olefins, 1-butene, 1-octene, decenes and principally 1-hexene, as well as the oligomerization solvent and C12+ by-products (i.e. products containing at least 12 carbon atoms per molecule). Said effluent also comprises catalyst.

One of the major problems in this field concerns the separation of 1-hexene from the other constituents of the mixture obtained from the ethylene trimerization reaction with a degree of purity that complies with the subsequent use of 1-hexene, for example as a co-monomer in the manufacture of polyethylene.

A certain number of procedures have been developed in order to improve the separation of 1-hexene while reducing the costs linked to the investment necessary to construct the facilities involved.

Typically, the oligomerization products may be separated using separation means such as distillation columns operating in series and based on differences in the boiling points of the compounds to be separated. Thus, the first distillation column separates the ethylene, the most volatile compound which leaves via the top of the column, the other heavier constituents leaving from the bottom of the column and supplying a second column in which 1-hexene is obtained.

As an example, the U.S. Pat. No. 7,476,775 describes a process for separating an oligomerization effluent comprising separating the effluent obtained from the oligomerization reaction into a liquid fraction and a gaseous fraction, and distillation of the liquid fraction and the gaseous fraction in order to recover the oligomerization product fractions.

The Applicant's U.S. Pat. No. 5,853,551 describes a layout for separating ethylene and 1-butene from C4+, then 1-butene from C6+, then hexene and octene from C10+ and solvent, and finally two separations, on the one hand 1-hexene and 1-octene and on the other hand solvent and C10+. U.S. Pat. No. 5,853,551 describes a layout which consists of adding supplemental 1-butene to the first distillation column in order to keep the temperature at the column bottom to values around which the alpha-olefins are stable and to be able to separate the ethylene with a little 1-butene at the top of the column.

The processes proposed in the prior art suffer from a disadvantage, in particular in terms of efficiency in the selectivity of the separation and energy efficiency. Thus, there continues to be a need for improvements to processes for separating the products of oligomerization, in particular the trimerization of ethylene for the production of 1-hexene.

The Applicant has developed a novel process for separating oligomerization products which can be used to overcome the problems cited above.

SUMMARY OF THE INVENTION

The present invention concerns a process for separating 1-hexene from a mixture obtained from an ethylene trimerization reaction section, said mixture comprising ethylene, solvent, ethylene trimerization catalyst and products formed, including 1-hexene, the process comprising at least the following steps:

a) separating the mixture obtained from the ethylene trimerization reaction in a first distillation column into a top fraction comprising ethylene and a bottom fraction;

b) separating, in at least one other distillation column, at least a portion of an effluent deriving from the bottom fraction obtained from step a) into a top fraction comprising 1-hexene and 1-butene and a bottom fraction;

c) separating, in a final distillation column, at least a portion of the fraction comprising 1-hexene and 1-butene obtained from step b) into a top fraction principally comprising 1-butene and into a bottom fraction principally comprising 1-hexene, and in said process:
    at least a portion of an effluent deriving from the bottom fraction obtained from step b) is returned to the reaction section and at least one other portion of said bottom fraction obtained from step b) is used in at least one recirculation loop connecting the reaction section and the column of said step b), said recirculation loop being used to cool the reaction section and to reboil said column of step b).

In a variation of the invention, at least a portion of an effluent deriving from the bottom fraction obtained from step b) is sent to at least one distillation column in order to eliminate a bottom fraction essentially comprising C8+ olefins therefrom before returning at least a portion of the top fraction obtained from said distillation column to the reaction section.

In another variation of the invention, at least a portion of an effluent deriving from the bottom fraction obtained from step a) is sent to at least one distillation column in order to eliminate a bottom fraction essentially comprising C8+ olefins therefrom before sending at least a portion of the top fraction obtained from said distillation column to the distillation column of step b).

Advantageously, in accordance with the process of the invention, at least a portion of an effluent deriving from the bottom fraction obtained from step b) is returned to the top of the first column of step a) in order to wash the ethylene leaving from the top of said first column and to entrain the C4+ olefins fraction towards the bottom of said first column.

Further characteristics and advantages of the invention will become apparent from the following detailed description.

DETAILED DESCRIPTION OF THE INVENTION

List of Figures

The description and the figures presented below can be used to illustrate the implementations of the process of the invention more clearly and to highlight the series of advantages associated with carrying out this process.

In the remainder of the text, reference will be made to the numerals indicated in FIGS. 1 and 2 for the purposes of clarity.

Reaction Section

The process of the invention comprises an ethylene trimerization reaction section. During the trimerization reaction, ethylene is brought into contact with an oligomerization catalyst in order to produce 1-hexene.

Catalysts which can be used to carry out the ethylene trimerization reaction can be heterogeneous or homogeneous with respect to the reaction medium. They generally comprise at least one of the following elements: a transition metal, an acidic compound or a basic compound.

In general, the various compounds are then separated into two portions, on the one hand the essential constituent of the activated catalyst which contains the principal metal, which is therefore usually termed the "catalyst", and the secondary constituents which act to activate the essential constituent and maintain its activity, and thus usually termed the "activator".

Advantageously, in accordance with the process of the invention, the various compounds involved in the preparation of the activated catalyst are stored in at least two different drums and the catalyst resulting from mixing them is stored in one drum. In one implementation of the process of the invention, the activated catalyst which is ready for use is transferred to a single drum which supplies the reactor. The catalyst and the activator are advantageously pumped separately at controlled flow rates in order to adjust the molar ratios between these different compounds. The ethylene trimerization reaction is exothermic. Thus, it is necessary to control the heat of reaction. Advantageously, this control of exothermicity is effected by means of one or more loops for recycling reaction medium by passing said reaction medium through at least one heat exchanger. Thus, the catalyst and the activator can be injected into the recycle loops of the reactor of the reaction section, preferably at two different regions.

Any ethylene trimerization catalyst may be used in the layout of the process of the invention. In particular, the catalysts described in patent application WO 07/039851 or in patent applications WO 04/056479, WO 03/053891 or WO 02/04119 may be used. The catalyst which can be used in the process of the invention may comprise a transition metal complex. This complex is formed by complexing a metal with at least one ligand comprising heteroatoms such as nitrogen, oxygen or phosphorus, which means that this metal can be dissolved in a hydrocarbon medium. The complex may, for example, be an organic oxygen-containing compound: ether, ester, acetal, ketal, etc.

Chromium-based catalysts are known to be highly active ethylene trimerization catalysts which lead to the formation of 1-hexene with good selectivity, i.e. with a little polyethylene and a small proportion of butenes. Examples of catalysts and activators which may be used in the process of the invention are mixtures of a chromium compound (catalyst) such as halides, carboxylates, acetylacetonates, aryloxy or alkoxy compounds, with an aryloxy compound of an element such as aluminium, magnesium, calcium, strontium or barium, and a hydrocarbylaluminium (activator). Examples of such catalysts and activators are described in patent FR 2 802 833. The hydrocarbylaluminium compound mentioned above may also be replaced by any hydrocarbyl compound of another element such as aluminium, gallium, niobium, tantalum, yttrium or a rare earth such as lanthanum. The hydrocarbyl compound may also be halogenated as described, for example, in patent application WO 2007/039851.

In accordance with the invention, the components of the activated catalyst are advantageously brought into contact with a solvent composed of at least one hydrocarbon selected from the following saturated hydrocarbons: hexane, cyclohexane, heptane, butane, toluene, ortho-xylene, isobutane, 2,2-dimethylpentane or from the following unsaturated hydrocarbons: mono-olefins or diolefins containing 4 to 10 carbon atoms or aromatic compounds such as benzene, toluene or xylenes, for example. More preferably, unsaturated hydrocarbons are used.

Advantageously, the solvent used is selected from 2,2-dimethylpentane, cyclohexane, toluene and ortho-xylene, and more preferably from 2,2-dimethylpentane and cyclohexane.

In accordance with the process of the invention, the ethylene trimerization reaction is carried out in one or more reactor(s). The reactor or reactors may be any means which is suitable and known to the skilled person. As an example, in the case of solid heterogeneous catalysts, it is possible to use fixed bed reactors, fluidized bed reactors, moving bed reactors, catalytic columns or reactors which can be used with homogeneous catalysts such as tube-in-shell reactors, stirred tank reactors, liquid/vapour equilibrium reactors, etc.

The ethylene trimerization reaction may be carried out in batches, semi-continuously or continuously. Preferably, it is carried out continuously.

In accordance with the process of the invention, the operating conditions for the trimerization reactor are such that the reaction medium is at the bubble point. This bubble point is ensured by continuously withdrawing vapour, generally with a small vapour flow rate (13) from the top of the reactor. Advantageously, in accordance with the invention, at least a portion of the vapour withdrawn from the reactor top 13 is sent, 14, to the distillation column 25. Preferably, said reactor is continuously stirred. Said stirring is promoted, inter alia, by a recycle loop 18, 18b to the reactor.

Advantageously, the temperature of the ethylene trimerization reaction is in the range 0° C. to 300° C., preferably in the range 30° C. to 210° C., more preferably in the range 100° C. to 180° C. The operating pressure is selected so as to maintain the reaction medium of the ethylene trimerization reaction at the bubble point. Said pressure is advantageously in the range 0.1 to 35 MPa, preferably in the range 1 to 20 MPa, and more preferably in the range 5 to 15 MPa.

In accordance with the process of the invention, from the outlet of the ethylene trimerization reaction section (reactor 12), the catalyst and its activator contained in the bottom fraction 21 leaving said reactor are advantageously neutralized by injecting an inhibitor 22. The mixture is generally produced using a dynamic in-line mixer or a static in-line mixer. The catalyst and its activator are neutralized using any compound which is known to the skilled person to have an inhibiting action on the trimerization catalyst. Said compound is generally selected from amines, preferably primary or secondary amines with general formula $R1R2NH$ in which $R1$ is hydrogen or a hydrocarbon radical and $R2$ is a hydrocarbon radical. Preferably, an inhibitor selected from the following compounds or their mixtures is used: cyclohexylamine, ethyl-2-hexylamine, arylamine, stearylamine, oleylamine, aniline, N-methyl aniline, dibutylamine, didecylamine, and mixtures of amines obtained from natural fats such as tallow, palm oil or coprah oil.

The inhibitor may also be selected from linear or branched alcohols preferably containing 2 to 20 carbon atoms, more preferably 5 to 15 carbon atoms. Highly preferably, the inhibitor is a branched alcohol comprising at least one hydrocarbyl branch, for example an alcohol comprising at least one methyl, ethyl, propyl or butyl branch attached to an alcohol chain preferably containing 2 to 16 carbon atoms, and highly preferably containing 4 to 10 carbon atoms. Preferably, the inhibitor is selected from the following alcohols or their mixtures: 1-hexanol, 2-hexanol, 3-hexanol, 2-methylhexanol, 2-ethylhexanol, 3-octanol, 1-heptanol, 2-heptanol, 3-heptanol, 4-heptanol, 2-methyl-3-heptanol, 1-octanol, 2-octanol, 3-octanol, 4-octanol, 7-methyl-2-decanol, 1-decanol, 2-decanol, 3-decanol, 4-decanol, 5-decanol and 2-ethyl-1-decanol.

The inhibitor is preferably added at the temperature at which the trimerization reaction takes place.

This step for neutralizing any catalytic activity in particular means that the presence of catalyst which is still active will not change the purity of the initial trimerization reaction products through an uncontrolled reaction.

The neutralized reaction medium obtained from the reactor 21 is then sent to a separation unit 23 in which on the one hand the neutralized catalyst as well as heavy by-products (C12+) from the reaction are separated on the other hand from unconverted ethylene, the other products formed and the solvent. In accordance with the invention, the fraction obtained from the separation unit 23 containing unconverted ethylene, the products formed and the solvent is sent in the vapour form, 24, to the distillation section. Separation in the separation unit 23 is advantageously carried out in a series of flash stages.

Advantageously, the pressure of the reaction medium obtained from the reactor 21 is reduced to a pressure in the range 2 to 5 MPa, preferably in the range 3 to 4.5 MPa. Said pressure-reduced reaction medium is then vaporized by heating to a temperature in the range 150° C. to 200° C., preferably in the range 160° C. to 190° C. Said vaporization is advantageously carried out in a heat exchanger. The vapour phase is then separated from the liquid phase in a drum. The vapour phase is sent to the distillation section and the liquid phase is sent to a second flash.

The pressure of the liquid phase resulting from the first flash is reduced to a pressure in the range 0.5 to 2 MPa, preferably in the range 0.8 to 1.5 MPa. Said pressure-reduced liquid phase is then vaporized by heating to a temperature in the range 160° C. to 220° C., preferably in the range 170° C. to 210° C. This vaporization is advantageously carried out in a heat exchanger. The vapour phase is then separated from the liquid phase in a drum. The vapour phase is sent to the distillation section and the liquid phase is sent to a third flash.

The pressure of the liquid phase resulting from the second flash is reduced to a pressure in the range 0.1 to 0.5 MPa. Said pressure-reduced liquid phase is then vaporized by heating to a temperature in the range 160° C. to 220° C. This vaporization is advantageously carried out in a heat exchanger, preferably a thin film or falling film exchanger.

The neutralized catalyst as well as the heavy by-products (C12+) separated in the separation unit 23 are pumped and sent, 38, to an incinerator.

Distillation Section

Typically, the molecular weight of the oligomeric olefins obtained from ethylene trimerization is higher than the unreacted ethylene. In general, the unreacted ethylene has a lower boiling point than that of the oligomers obtained from the trimerization reaction, including 1-hexene.

In accordance with the invention, any separation means known to the skilled person which can exploit these volatility differences and molecular weight differences between the products to be separated may be employed. Advantageously, in accordance with the invention, the separation means employed are distillation columns of any type.

In accordance with the process of the invention, the fraction obtained from the separation unit 23, namely: unconverted ethylene, the products formed and the solvent, is sent to the distillation section in the vapour form, 24.

The distillation section advantageously comprises at least three distillation columns, preferably at least four distillation columns. In a preferred variation of the invention, the distillation section comprises four distillation columns.

Step a)

In accordance with the invention, the fraction obtained from the separation unit 23, namely: unconverted ethylene, the products formed and the solvent, undergoes a separation step a). Said fraction is sent in the vapour form, 24, to a first distillation column 25 in which the unconverted ethylene is separated as a top fraction from the remainder of the compounds in the bottom fraction.

Advantageously, in accordance with the invention, the distillation column of separation step a) is operated at a pressure in the range 0.1 to 1.5 MPa, preferably in the range 0.5 to 1 MPa, a column top temperature in the range 0° C. to 100° C., preferably in the range 40° C. to 80° C., and a column bottom temperature in the range 100° C. to 300° C., preferably in the range 140° C. to 220° C. Preferably, the ethylene separated at the column top at 25 is sent to the reaction section 12.

Advantageously in accordance with the process of the invention, the ethylene separated at the top of column 25 is returned (7, 9, 11) at the same time as at least the supply of hydrogen, 4, and fresh ethylene 1. The ethylene separated at the column top of the column 25, hydrogen and fresh ethylene are advantageously mixed in at least one recycle compressor (reference numerals 10 or 8 in FIGS. 1 and 2). In accordance with the invention, the mixture is introduced into the reactor 12 using a distributor in order to provide good dispersion of the droplets of ethylene within the reaction medium (not shown in the figures). The ethylene may also be introduced into at least one of the recycle loops of the process of the invention.

Preferably, in order to avoid removing heat in order to condense the column top of the first column of step a), at least a portion of an effluent deriving from the bottom fraction obtained from step b) is returned to the top of said first column of step a) in order to wash the ethylene leaving from the top of said first column and to entrain the C4+ olefin fraction towards the bottom of said first column. In fact, the bottom fraction obtained from step b) is principally composed of solvent (at least 95% by weight of solvent). This solvent can be used to preferentially absorb the heavy products and entrain them towards the bottom of the column.

Step b)

In accordance with the invention, at least a portion of an effluent deriving from the bottom fraction obtained from step a) then undergoes a separation step b) in which at least a portion of said effluent deriving from said bottom fraction obtained from step a) is separated, in at least one other distillation column 30, into a top fraction 31 comprising 1-hexene and 1-butene and a bottom fraction. Said bottom fraction is principally composed of solvent. Advantageously, the quantity of solvent in this fraction is 95% by weight or more, preferably more than 98% by weight and more preferably 99.5% by weight or more.

Advantageously, in accordance with the invention, the distillation column of separation step b) is operated at a pressure in the range 0 to 0.5 MPa, preferably in the range 0.01 to 0.3 MPa, a column top temperature in the range 20° C. to 150° C., preferably in the range 40° C. to 100° C., and a column bottom temperature in the range 50° C. to 200° C., preferably in the range 80° C. to 150° C.

In accordance with the invention, at least a portion of an effluent deriving from the bottom fraction obtained from step b) is sent, 37, to the reaction section and at least another portion of said bottom fraction obtained from step b) is used in a recirculation loop 19 between the reaction section and said other column of said step b) in order to cool the reaction section and reboil the column of said step b). Advantageously, in accordance with the invention, said other portion of said bottom fraction obtained from step b) is removed either from the bottom of the column 30, or via a side stream preferably located close to the bottom of the column, and more preferably via a side stream located in the lower quarter of said column.

The ethylene trimerization reaction is in fact exothermic. The heat generated by the reaction has to be extracted in order to avoid an uncontrolled rise in the temperature of the reaction medium. Depending on the temperature reached, the consequences are a loss of selectivity by thermal degradation of the catalyst and the reaction products. In accordance with the invention, the heat of reaction generated in the reactor 12 is extracted using at least one recirculation loop using at least a portion of an effluent deriving from the bottom fraction obtained from step b). The heat generated in the reactor is extracted from the reactor via a recycle loop 18, 18b. The recycle loop 18, 18b of the reactor preferably uses exchangers, preferably of the kettle type 17, to transfer the heat generated in the reactor 12 to the effluent deriving from the bottom fraction obtained from step b) causing vaporization of said effluent deriving from said bottom fraction.

In accordance with the invention, the portion of the effluent deriving from said bottom fraction obtained from step b) vaporized at the outlet from the exchanger 17 is returned at 20 to the distillation column of step b), 30, closing the recirculation loop. The return of the fraction 20 to the distillation column of step b) acts as a side reboiler to lighten the load on the principal reboiler of the distillation column for step b), with a consequent saving on steam.

Controlling the vaporization pressure of the bottom fraction obtained from step b) in the exchanger of the recirculation loop and of the recycle loop of the reactor means that the mean difference in temperature between the hot and cold streams can be adjusted, and thus the exchange capacity of the exchangers can be adjusted. Advantageously, a kettle type exchanger is used.

A further advantage of the recirculation loop is that it can be used to control the exothermicity of the trimerization reaction in the reactor 12, but it also can ensure that said reactor is continuously stirred. The recirculation loop can be used to ensure, at the same time:

that heat released by the reaction is evacuated; in the prior art, this is carried out, for example, by vaporizing water in a kettle type exchanger. The pressure of this generated water vapour is too low to be used efficiently in the process. The water vapour produced thereby thus has to be condensed in a supplemental exchanger (for example an air exchanger) in order to be recycled to the kettle type exchanger. Cooling this vapour represents a high energy consumption and the associated equipment (exchanger, drum, pump) represents an additional investment cost;

the majority of the reboil of the bottom of the column 30 of step b); in the prior art, this is carried out by means of an exchanger, for example, with steam being used as the hot fluid, for example. Production of this vapour represents a high energy consumption and the equipment associated with producing it (boiler, pump, water treatment) also represents a high investment cost.

In accordance with the invention, the quantities of heat to be exchanged in order to cool the reaction medium and to vaporize a bottom fraction from the column of step b) in order to reboil it are substantially similar—the advantage of this is effective thermal integration.

The process of the invention has the advantage of providing energy savings on the one hand since it consumes less steam, and economic savings on the other hand by reducing equipment costs.

In order to prevent an accumulation of C8+ hydrocarbons in the unit, it is preferable to extract them with the aid of a supplemental distillation column which may be incorporated into the layout of the process in at least two different locations.

Figure 1:
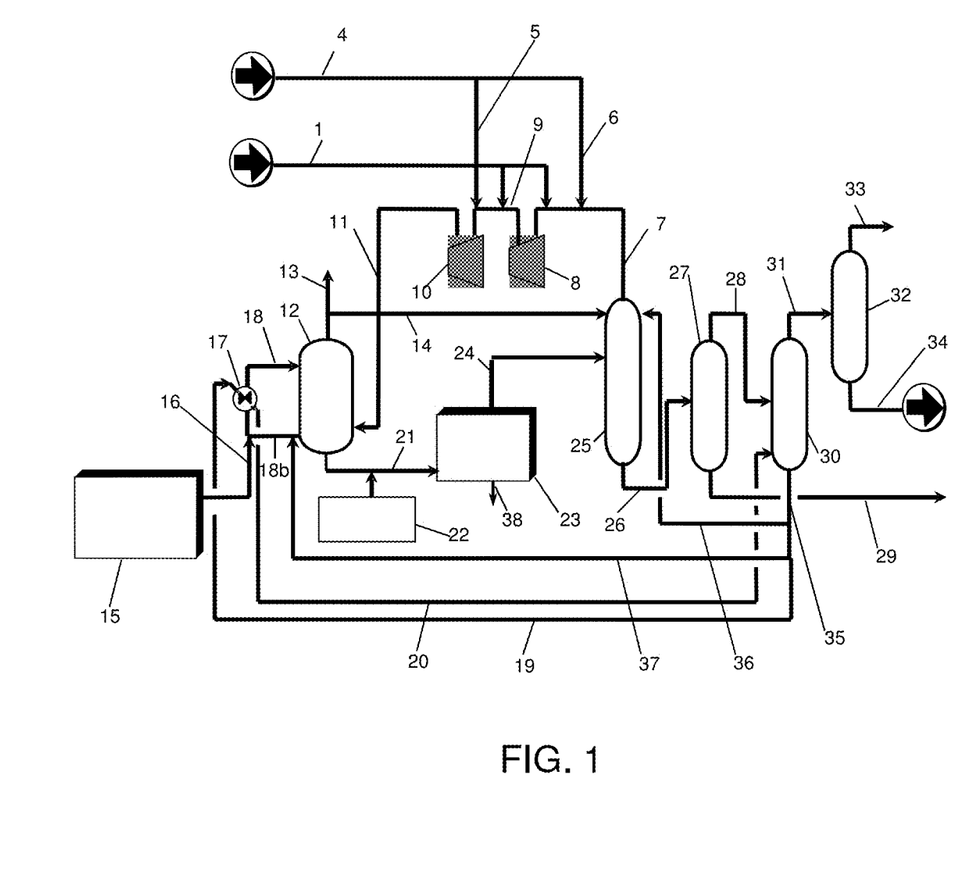
FIG. 1 is a non-limiting illustration of an implementation in which at least a portion of the bottom fraction obtained from step a) is sent to a distillation column in order to eliminate a C8+ fraction therefrom before being sent to the distillation column of step b).

In a preferred variation of the process of the invention as illustrated in FIG. 1, at least a portion of an effluent deriving from the bottom fraction obtained from step a) is sent to at least one distillation column 27 to eliminate a bottom fraction 29 essentially comprising C8+ olefins therefrom before sending the top fraction 28 obtained from said distillation column to the distillation column of step b) (column 30). Advantageously, in accordance with the invention, said distillation column is operated at a pressure in the range 0 to 1 MPa, preferably in the range 0.1 to 0.5 MPa, a column top temperature in the range 60° C. to 160° C., preferably in the range 90° C. to 130° C., and a column bottom temperature in the range 100° C. to 300° C., preferably in the range 170° C. to 240° C. In this variation, the fresh catalyst 16 and at least a portion of an effluent deriving from the bottom fraction obtained from step b), 37, are mixed with the liquid pumped from the reactor 12 in the recycle loop of the reactor 18b. The stream 16 and the stream 37 are introduced on the "tube" side of the exchanger. In accordance with the invention, at least another portion of said bottom fraction obtained from the corresponding step b) is introduced into the recirculation loop on the "shell" side of the exchanger.

Figure 2:
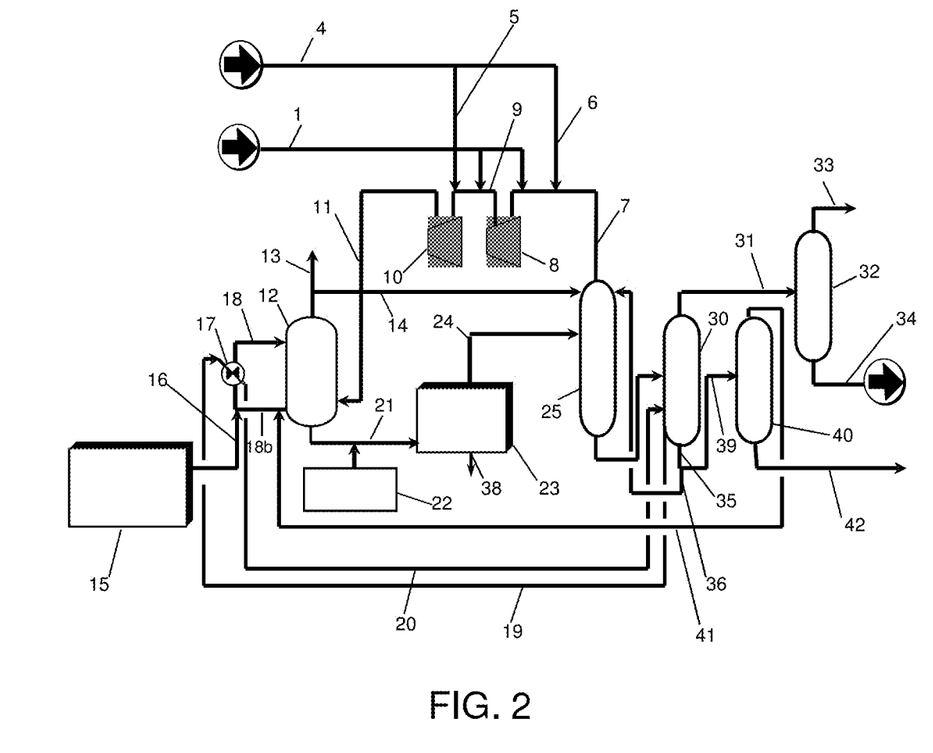
FIG. 2 is a non-limiting illustration of an implementation in which at least a portion of an effluent deriving from the bottom fraction obtained from step b) is sent to at least one distillation column in order to eliminate a bottom fraction essentially comprising C8+ olefins therefrom before returning at least a portion of the top fraction obtained from said distillation column to the reaction section.

In another variation of the process of the invention as illustrated in FIG. 2, at least a portion of an effluent deriving from the bottom fraction obtained from step b) (column 30) is sent to at least one distillation column (column 40) in order to eliminate a bottom fraction essentially comprising C8+ olefins therefrom before sending the top fraction 41 obtained from said distillation column to the reaction section. In accordance with this variation, the fresh catalyst 16 and the top fraction 41 are advantageously mixed, in the recycle loop of the reactor 18b, with liquid pumped from the reactor 12 and introduced into the "tube" side of the exchanger 17. Advantageously, in accordance with the invention, said distillation column is operated at a pressure in the range 0.05 to 1 MPa, preferably in the range 0.1 to 0.5 MPa, a column top temperature in the range 70° C. to 150° C., preferably in the range 90° C. to 130° C., and a column bottom temperature in the range 100° C. to 300° C., preferably in the range 150° C. to 220° C. Said top fraction obtained from said distillation column is principally composed of solvent. Advantageously, the quantity of solvent of this top fraction is 95% by weight or more, preferably more than 98% by weight and more preferably 99.5% by weight or more.

Step c)

In accordance with the invention, at least a portion of the top fraction 31 obtained from step b) undergoes a step c) in which said fraction essentially comprising 1-hexene and 1-butene obtained from step b) is separated, in a final distillation column 32, into a top fraction principally comprising 1-butene, 33, and into a bottom fraction principally comprising 1-hexene, 34. Advantageously, in accordance with the invention, said distillation column of the separation step c) is operated at a pressure in the range 0.5 to 1.5 MPa, preferably in the range 0.7 to 1.2 MPa, a column top temperature in the range 30° C. to 130° C., preferably in the range 50° C. to 90° C., and a column bottom temperature in the range 100° C. to 300° C., preferably in the range 130° C. to 200° C.

DETAILED DESCRIPTION OF THE FIGURES

Several implementations of the process of the invention are illustrated in FIGS. 1 and 2 for the purposes of better comprehension. These implementations are given by way of examples and are not limiting in nature. These illustrations of the process of the invention do not include details of all of the components necessary to carry it out. Only the elements necessary for understanding the invention are represented therein; the skilled person would be capable of completing these representations in order to carry out the invention.

FIG. 1 illustrates, in a non-limiting manner, an implementation in which at least a portion of the bottom fraction obtained from step a) is sent to a distillation column to eliminate a C8+ fraction therefrom before being sent to the distillation column of step b).

Fresh ethylene feed is supplied via a line 1 to an ethylene trimerization reactor 12. In accordance with FIG. 1, hydrogen 4 and/or fresh ethylene 1 is (are) mixed with ethylene 7 at the intermediate stage 9 of the recycle compressors 8, 10 or to the intake 7 of the first stage of a compressor 8. The catalyst and the activator prepared and stored in the drum 15 are injected into the reactor 12 via the line 16, more precisely to the level of the recycle loop of the reactor 18b, 18.

The product of the ethylene trimerization reaction is evacuated via the bottom of the reactor 12 via a line 21, in order to send it to a separation unit 23. The reactor bottoms 12, in particular activated catalyst, are neutralized by injecting an inhibitor 22 into the line 21. The mixture is generally formed using a dynamic in-line mixer. In the separation unit 23, neutralized catalyst as well as heavy by-products (C12+) are evacuated in the bottom fraction 38. The fraction comprising unconverted ethylene, the other products formed and the solvent is sent to the first distillation column 25 of step a) in the vapour form via the line 24. This separation step, with reference numeral 23, is generally constituted by one or more successive flash drums (drum separators with a liquid-vapour equilibrium) with intermediate steps for heating via heat exchangers.

In general and independently of FIG. 1, the vapour fraction obtained from the separation unit 23 (line 24) is separated in the first distillation column 25 into a top fraction 7 essentially comprising unconverted ethylene and a bottom fraction comprising C4+ olefins. In general and independently of FIG. 1, the bottom fraction obtained from the distillation column 25 is then sent directly via the line 26 to a distillation column 30 in which on the one hand a top fraction 31 comprising essentially 1-hexene and butene and on the other hand a bottom fraction 35 comprising the remainder of the products and the solvent are separated.

In the variation of the invention represented in FIG. 1, the effluent deriving from the bottom fraction obtained from the distillation column 25 is initially sent to another intermediate distillation column 27 in which a top fraction 28 (which is sent to the distillation column 30) is separated from a bottom fraction comprising C8+ products which are evacuated via a line 29. This intermediate column is not indispensable to the invention, but is an advantageous variation of the process of the invention in certain applications.

At least a portion of an effluent deriving from the bottom fraction obtained from column 30 is returned to the top of the first distillation column 25 via a line 36. At least a portion of an effluent deriving from the bottom fraction obtained from the column 30 is returned to the reactor via the line 37, more precisely to the recycle loop of the reactor 18b, 18. At least another portion of the effluent deriving from the bottom fraction obtained from column 30 is used in a recirculation loop (lines 19, 20) in order to cool the reaction section by means of the exchanger 17. The vaporized portion of the recirculating fraction (leaving the exchanger 17) is returned to the column 30 to reboil it. The top fraction 31 obtained from the distillation column 30 is sent to a final distillation column 32 in which a top fraction 33 essentially comprising 1-butene is separated from a bottom fraction essentially comprising the desired end product, namely 1-hexene, which is evacuated via the line 34.

FIG. 2 represents another implementational variation of the process of the invention in which there is no intermediate distillation column (reference numeral 27, FIG. 1). In column 30, on the one hand a top fraction 31 essentially comprising 1-hexene and butene and on the other hand a bottom fraction 35 comprising the remainder of the products and the solvent are separated. At least a portion of an effluent deriving from the bottom fraction obtained from column 30 is used in a recirculation loop (lines 19, 20) in order to cool the reaction section 12 via the exchanger 17. The vaporized portion of the recirculating fraction (leaving the exchanger 17) is sent to the column 30 for reboiling.

At least another portion of the effluent deriving from the bottom fraction obtained from the distillation column 30 is returned to the first distillation column 25 via the line 36. The top fraction 31 obtained from the distillation column 30 is sent to a final distillation column 32 in which a top fraction 33 essentially comprising 1-butene and a bottom fraction essentially comprising the final desired product is obtained, namely 1-hexene, which is evacuated via the line 34.

A third distillation column 40 receives, via the line 39, another portion of the effluent deriving from the bottom fraction obtained from the distillation column 30 (35). The top fraction obtained from the column 40 (essentially composed of solvent) is returned to the reactor 12 via a line 41, more precisely in the recycle loop of the reactor 18b, 18. The bottom fraction obtained from the column 40 comprising C8+ olefins is evacuated via the line 42.

The following examples illustrate the present invention without in any way limiting the scope.

EXAMPLES

Example 1 (in Accordance with the Invention)

The process layout used was that of FIG. 1.

The feed 1 used was composed of polymer grade ethylene (i.e. approximately 99.9% ethylene). The catalytic system used in the oligomerization reactor 12 comprised the following elements: chromium tris (2-ethylhexanoate), bis (2,6-diphenylphenoxy) magnesium, and triethylaluminium in the following molar proportions: 1/1/3. The inhibitor used was 2-ethylhexanol. These constituent elements of the catalyst were brought into contact in dry, deaerated cyclohexane (solvent). The reactor was operated at 135° C. and at the bubble point. The reactor temperature was kept constant. The heat of the reaction was eliminated via the recycle loop 18, 18b and the exchanger 17 which was used to exchange heat with the recirculation loop 19, 20.

The column 25 was operated in accordance with rules known to the skilled person so as to separate the residual ethylene from the solvent and the reaction products.

The column 27 could be used to separate, at the column bottom, a cut containing the C8+ olefins and the solvent, 1-hexene and 1-butene at the column top. It was operated at a pressure of 0.23 MPa at the column top, a column top temperature of 108° C. and a column bottom temperature of 190° C.

The column 30 was used to separate the 1-butene and the 1-hexene from the solvent. It was operated with a column top temperature of 75° C. and a column bottom temperature of 110° C. The column top pressure was 0.15 MPa.

The column 32 was used to separate the 1-hexene produced at the column bottom and a cut which was rich in 1-butene at the column top. It was operated at a pressure of 1.06 MPa at the column top, a column top temperature of 73° C. and a column bottom temperature of 165° C.

After separation in the columns 25, 27, 30 and 32, 0.86 tonnes of 1-hexene (34), 0.015 tonnes of a cut which was rich in 1-butene (33) and 0.066 tonnes of a cut which was rich in C8+ (29) per tonne of ethylene introduced via the line 1 were produced.

1.12 tonnes of low pressure steam (0.4 MPa) per tonne of feed was necessary to operate reboiling of the column 30.

Example 2 (Comparative)

Like Example 1, the solvent used was cyclohexane.

The process carried out was distinguished from that carried out in Example 1 in that the exchanger 17 was not supplied with solvent separated from the distillation column 30, but with water. Thus, there was no need to return the solvent to the column 30 after exchange.

The exchanger 17 was supplied with water which was vaporized. Very low pressure steam (0.17 MPa) was then produced which could not be upgraded in another part of the process. Thus, this vapour was condensed, pumped and recycled to the exchanger 17.

The columns 25, 27, 30 and 32 were operated under the same conditions as for Example 1.

After separation in the columns 25, 27, 30 and 32, 0.86 tonnes of 1-hexene (34), 0.015 tonnes of a cut which was rich in 1-butene (33) and 0.066 tonnes of a C8+ cut (29) per tonne of feed (ethylene) were produced.

1.75 tonnes of low pressure steam (0.4 MPa) per tonne of feed was necessary in order to reboil the column 30. Compared with the process of the invention of Example 1, it is apparent that a supplemental 0.63 tonnes of low pressure steam (0.4 MPa) per tonne of feed was necessary.

Example 3 (in Accordance with the Invention)

The process used differed from that of Example 1 in that the solvent used was 2,2-dimethylpentane.

The column 25 was operated in accordance with rules known to the skilled person so as to separate the residual ethylene from the solvent and the reaction products.

The column 27 was operated at a pressure of 0.23 MPa at the column top, a column top temperature of 107° C. and a column bottom temperature of 191° C.

The column 30 was operated with a column top temperature of 76° C. and a column bottom temperature of 108° C. The column top pressure was 0.15 MPa.

The column 32 was operated at a pressure of 1.06 MPa at the column top, a column top temperature of 73° C. and a column bottom temperature of 165° C.

After separation in the columns 25, 27, 30 and 32, 0.86 tonnes of 1-hexene (34), 0.015 tonnes of a cut which was rich in 1-butene (33) and 0.066 tonnes of a C8+ cut (29) per tonne of ethylene introduced via the line were produced.

1.04 tonnes of low pressure steam (0.4 MPa) per tonne of feed was necessary to operate reboiling of the column 30.

Example 4 (Comparative)

Like Example 3, the solvent used was 2,2-dimethylpentane.

The process carried out was distinguished from that carried out in Example 3 in that the exchanger 17 was not supplied with solvent separated from the distillation column 30, but with water. Thus, there was no need to return the solvent to the column 30 after exchange.

The exchanger 17 was supplied with water which was vaporized. Very low pressure steam (0.17 MPa) was then produced which could not be upgraded in another part of the process. Thus, this vapour was condensed, pumped and recycled to the exchanger 17.

The columns 25, 27, 30 and 32 were operated under the same conditions as for Example 3.

After separation in the columns 25, 27, 30 and 32, 0.86 tonnes of 1-hexene (34), 0.015 tonnes of a cut which was rich in 1-butene (33) and 0.066 tonnes of a C8+ cut (29) per tonne of feed (ethylene) were produced.

1.67 tonnes of low pressure steam (0.4 MPa) per tonne of feed was necessary in order to reboil the column 30. Compared with the process of the invention of Example 3, it is apparent that a supplemental 0.63 tonnes of low pressure steam (0.4 MPa) per tonne of feed was necessary.

Example 5 (in Accordance with the Invention)

The process layout used was that of FIG. 1.

The feed 1 used was composed of polymer grade ethylene (i.e. approximately 99.9% ethylene). The catalytic system used in the oligomerization reactor 12 comprised the following elements: chromium tris (2-ethylhexanoate), bis (2-tert-butyl-6-phenylphenoxy) magnesium, and triethylaluminium in the following molar proportions: 1/1/3. The inhibitor used was 2-ethylhexanol. These constituent elements of the catalyst were introduced into dry, deaerated cyclohexane (solvent). The reactor was operated at 135° C. and at the bubble point. The reactor temperature was kept constant. The heat of the reaction was eliminated via the recycle loop 18, 18b and the exchanger 17 which was used to exchange heat with the recirculation loop 19, 20.

The column 25 was operated in accordance with rules known to the skilled person so as to separate the residual ethylene from the solvent and the reaction products.

The column 27 could be used to separate, at the column bottom, a cut containing the C8+ olefins and the solvent, 1-hexene and 1-butene at the column top. It was operated at a pressure of 0.23 MPa at the column top, a column top temperature of 108° C. and a column bottom temperature of 190° C.

The column 30 was used to separate the 1-butene and the 1-hexene from the solvent. It was operated with a column top temperature of 75° C. and a column bottom temperature of 110° C. The column top pressure was 0.15 MPa.

The column 32 was used to separate the 1-hexene produced at the column bottom and a cut which was rich in 1-butene at the column top. It was operated at a pressure of 1.06 MPa at the column top, a column top temperature of 73° C. and a column bottom temperature of 165° C.

After separation in the columns 25, 27, 30 and 32, 0.87 tonnes of 1-hexene (34), 0.007 tonnes of a cut which was rich in 1-butene (33) and 0.064 tonnes of a C8+ cut (29) per tonne of feed (ethylene) were produced.

1.13 tonnes of low pressure steam (0.4 MPa) per tonne of feed was necessary to operate reboiling of the column 30.

Example 6 (Comparative)

Like Example 5, the solvent used was cyclohexane.

The process carried out was distinguished from that carried out in Example 5 in that the exchanger 17 was not supplied with solvent separated from the distillation column 30, but with water. Thus, there was no need to return the solvent to the column 30 after exchange.

The exchanger 17 was supplied with water which was vaporized. Very low pressure steam (0.17 MPa) was then produced which could not be upgraded in another part of the process. This vapour was condensed, pumped and recycled to the exchanger 17.

The columns 25, 27, 30 and 32 were operated under the same conditions as for Example 5.

After separation in the columns 25, 27, 30 and 32, 0.87 tonnes of 1-hexene (34), 0.007 tonnes of a cut which was rich in 1-butene (33) and 0.064 tonnes of a C8+ cut (29) per tonne of feed (ethylene) were produced.

1.76 tonnes of low pressure steam (0.4 MPa) per tonne of feed was necessary in order to reboil the column 30. Compared with the process of the invention of Example 5, it is apparent that a supplemental 0.63 tonnes of low pressure steam (0.4 MPa) per tonne of feed was necessary.

Example 7 (in Accordance with the Invention)

The process used differed from that of Example 5 in that the solvent used was toluene.

The reactor was operated at 165° C. and at the bubble point. The reactor temperature was kept constant.

The column 25 was operated in accordance with rules known to the skilled person so as to separate the residual ethylene from the solvent and the reaction products.

The column 27 was operated at a pressure of 0.23 MPa at the column top, a column top temperature of 136° C. and a column bottom temperature of 205° C.

The column 30 was operated with a column top temperature of 76° C. and a column bottom temperature of 140° C. The column top pressure was 0.15 MPa.

The column 32 was operated at a pressure of 1.06 MPa at the column top, a column top temperature of 73° C. and a column bottom temperature of 165° C.

After separation in the columns 25, 27, 30 and 32, 0.87 tonnes of 1-hexene (34), 0.007 tonnes of a cut which was rich in 1-butene (33) and 0.064 tonnes of a C8+ cut (29) per tonne of feed (ethylene) were produced.

No low pressure steam had to be added in order to operate the reboiling of the column 30.

Example 8 (Comparative)

Like Example 7, the solvent used was toluene.

The process carried out was distinguished from that carried out in Example 7 in that the exchanger 17 was not supplied with solvent separated from the distillation column 30, but with water. Thus, there was no need to return the solvent to the column 30 after exchange.

The exchanger 17 was supplied with water which was vaporized. Very low pressure steam (0.17 MPa) was then produced which could not be upgraded in another part of the process. Thus, this vapour was condensed, pumped and recycled to the exchanger 17.

The reactor was operated at 165° C. and at the bubble point. The reactor temperature was kept constant.

The column 25 was operated in accordance with rules known to the skilled person so as to separate the residual ethylene from the solvent and the reaction products.

The column 27 was operated at a pressure of 0.23 MPa at the column top, a column top temperature of 136° C. and a column bottom temperature of 205° C.

The column 30 was operated with a column top temperature of 76° C. and a column bottom temperature of 140° C. The column top pressure was 0.15 MPa.

The column 32 was operated at a pressure of 1.06 MPa at the column top, a column top temperature of 73° C. and a column bottom temperature of 165° C.

After separation in the columns 25, 27, 30 and 32, 0.87 tonnes of 1-hexene (34), 0.007 tonnes of a cut which was rich in 1-butene (33) and 0.064 tonnes of a C8+ cut (29) per tonne of feed (ethylene) were produced.

0.61 tonnes of low pressure steam (0.4 MPa) per tonne of feed was necessary in order to reboil the column 30. Compared with the process of the invention of Example 7, it is apparent that a supplemental 0.61 tonnes of low pressure steam (0.4 MPa) per tonne of feed was necessary.

The entire disclosures of all applications, patents and publications, cited herein and of corresponding French Application No. 12/01886, filed Jul. 4, 2012 are incorporated by reference herein.

The invention claimed is:

1. A process for separating 1-hexene from a mixture obtained from an ethylene trimerization reaction section, said mixture comprising ethylene, solvent, ethylene trimerization catalyst and products formed, including 1-hexene, the process comprising:

a) separating the mixture obtained from the ethylene trimerization reaction section in a first distillation column into a top fraction comprising ethylene and a bottom fraction;

b) separating, in at least one other distillation column, at least a portion of an effluent deriving from the bottom fraction obtained from step a) into a top fraction comprising 1-hexene and 1-butene and a bottom fraction;

c) separating, in a final distillation column, at least a portion of the fraction comprising 1-hexene and 1-butene obtained from step b) into a top fraction principally comprising 1-butene and into a bottom fraction principally comprising 1-hexene, and in said process:

at least a portion of an effluent deriving from the bottom fraction obtained from step b) is returned to the ethylene trimerization reaction section and at least one other portion of said bottom fraction obtained from step b) is used in at least one recirculation loop connecting the ethylene trimerization reaction section and the column of said step b), said recirculation loop being used to cool the ethylene trimerization reaction section and to reboil said column of step b).

2. A process according to claim 1, in which at least a portion of an effluent deriving from the bottom fraction obtained from step b) is sent to at least one distillation column in order to eliminate a bottom fraction essentially comprising C8+ olefins therefrom before returning at least a portion of the top fraction obtained from said distillation column to the ethylene trimerization reaction section.

3. A process according to claim 1, in which at least a portion of an effluent deriving from the bottom fraction obtained from step a) is sent to at least one distillation column in order to eliminate a bottom fraction essentially comprising C8+ olefins therefrom before sending at least a portion of the top fraction obtained from said distillation column to the distillation column of step b).

4. A process according to claim 1, in which at least a portion of an effluent deriving from the bottom fraction obtained from step b) is returned to the top of the first column of step a) in order to wash the ethylene leaving from the top of said first column and to entrain the C4+ olefins fraction towards the bottom of said first column.

5. A process according to claim 1, in which the unreacted ethylene separated from the first distillation column of step a) is returned to the ethylene trimerization reaction section.

6. A process according to claim 5, in which fresh ethylene is mixed with the ethylene returned to the reaction section.

7. A process according to claim 5, in which hydrogen is mixed with the unreacted ethylene returned to the ethylene trimerization reaction section.

8. A process according to claim 1, in which the ethylene trimerization reaction section comprises at least one trimerization reactor.

9. A process according to claim 8, in which the operating conditions for the trimerization reactor are such that the reaction medium is at the bubble point.

10. A process according to claim 9, in which vapour (13) is continuously withdrawn from the top of the trimerization reactor.

11. A process according to claim 10, in which at least a portion of the vapour withdrawn from the top of the reactor (13) is sent (14) to the distillation column of step a).

12. A process according to claim 1, in which the ethylene trimerization reaction is operated at a temperature in the range 0° C. to 300° C. and a pressure in the range 0.1 to 35 MPa.

13. A process according to claim 1 wherein the catalyst contained in the mixture obtained from the ethylene trimerization reaction section is neutralized by injecting an inhibitor.

14. A process according to claim 13, in which at least a portion of the neutralized bottom fraction (21) is sent to a separation unit (23) in which on the one hand the neutralized catalyst as well as the heavy by-products (C12+) of the reaction are separated from unconverted ethylene, the other products formed and the solvent on the other hand.

15. A process according to claim 14, in which the separation is carried out in a series of flash stages.

* * * * *